United States Patent
Fisher et al.

(10) Patent No.: US 10,994,063 B2
(45) Date of Patent: *May 4, 2021

(54) BLOOD FILTERING COMPONENT, APPARATUS, AND METHOD

(71) Applicant: Sisu Global Health, Inc., Baltimore, MD (US)

(72) Inventors: Theresa Fisher, Lakewood, CO (US); Gene Parunak, Saline, MI (US); Rick Routson, Ypsilanti, MI (US); Steve Meines, Ypsilanti, MI (US); Gillian Henker, Baltimore, MD (US); Caitlin Winget, Shelburne, VT (US); Rajen Kumar, Troy, MI (US)

(73) Assignee: Sisu Global Health, Inc., Baltimore, MD (US)

(*) Notice: Subject to any disclaimer, the term of this patent is extended or adjusted under 35 U.S.C. 154(b) by 58 days.

This patent is subject to a terminal disclaimer.

(21) Appl. No.: 16/266,566

(22) Filed: Feb. 4, 2019

(65) Prior Publication Data
US 2019/0167871 A1 Jun. 6, 2019

Related U.S. Application Data

(63) Continuation of application No. 15/018,800, filed on Feb. 8, 2016, now Pat. No. 10,195,320, which is a
(Continued)

(51) Int. Cl.
*A61M 1/02* (2006.01)
*B01D 35/30* (2006.01)
(Continued)

(52) U.S. Cl.
CPC ........ *A61M 1/0281* (2013.01); *A61M 1/0005* (2013.01); *A61M 1/0056* (2013.01);
(Continued)

(58) Field of Classification Search
CPC combination set(s) only.
See application file for complete search history.

(56) References Cited

U.S. PATENT DOCUMENTS

| 472,547 A | 4/1892 | Nordtmeyer |
| 2,436,077 A | 2/1948 | Robertson |
| (Continued) | | |

FOREIGN PATENT DOCUMENTS

| DE | 3533936 A1 | 3/1987 |
| DE | 4132480 A1 | 4/1993 |

OTHER PUBLICATIONS

International Search Report re PCT/US16/35113 dated Oct. 13, 2016 (4 pages).
Written Opinion re PCT/US16/35113 dated Oct. 13, 2016 (5 pages).

*Primary Examiner* — Terry K Cecil
(74) *Attorney, Agent, or Firm* — Aurora Consulting LLC

(57) ABSTRACT

An apparatus including a hollow body, an inlet fluidly coupled to the hollow body, a piston slidably engaged within the hollow body, and a filter module arranged within the hollow body between the inlet and piston. The piston and hollow body cooperatively generate a negative pressure, relative to ambient, within the hollow body during distal piston translation from a first position to a second position, thereby drawing a fluid, such as blood, through the filter module into the hollow body. The piston and hollow body cooperatively generate a positive pressure, relative to ambient, within the hollow body during piston translation from the second position to the first position to egress the filtered fluid from the hollow body. The filter module may include a filter housing, a filter medium disposed within the housing, and a body valve configured to seal an open distal face of the filter housing.

19 Claims, 11 Drawing Sheets

Related U.S. Application Data continuation-in-part of application No. 13/445,837, filed on Apr. 12, 2012, now Pat. No. 9,254,352.

(60) Provisional application No. 62/276,817, filed on Jan. 8, 2016.

(51) Int. Cl.
*A61M 1/00* (2006.01)
*A61M 5/31* (2006.01)
*A61M 5/165* (2006.01)

(52) U.S. Cl.
CPC ........... *A61M 5/3145* (2013.01); *B01D 35/30* (2013.01); *A61M 2005/1657* (2013.01); *B01L 2300/0681* (2013.01); *B01L 2400/0638* (2013.01)

(56) References Cited

U.S. PATENT DOCUMENTS

| | | | |
|---|---|---|---|
| 3,661,265 A | 5/1972 | Greenspan | |
| 3,931,010 A | 1/1976 | Ayres et al. | |
| 6,143,174 A | 11/2000 | Graus | |
| 6,471,069 B2 | 10/2002 | Lin et al. | |
| 6,796,965 B2* | 9/2004 | Dumaresq-Lucas | A61M 5/3145 604/190 |
| 7,819,846 B2* | 10/2010 | Lee | A61M 5/3145 604/190 |
| 9,254,352 B2 | 2/2016 | Kumar et al. | |
| 10,195,320 B2* | 2/2019 | Fisher | A61M 1/0281 |
| 2006/0191841 A1 | 8/2006 | Kawarabata et al. | |
| 2010/0038305 A1* | 2/2010 | Ferguson | B01D 46/528 210/455 |
| 2010/0297577 A1 | 11/2010 | Cohen | |
| 2013/0174525 A1 | 7/2013 | Palmerton et al. | |
| 2013/0270161 A1 | 10/2013 | Kumar et al. | |

* cited by examiner

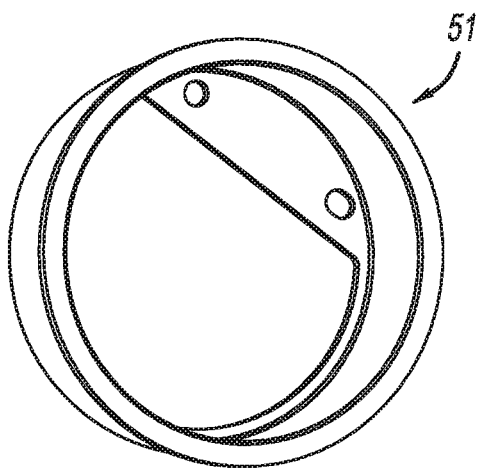
FIG-9A
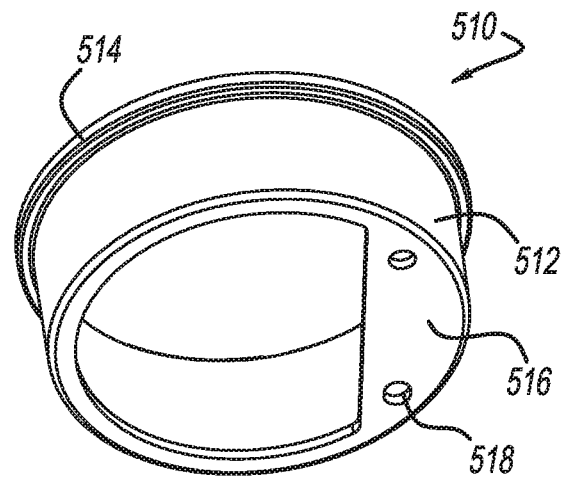
FIG-9B
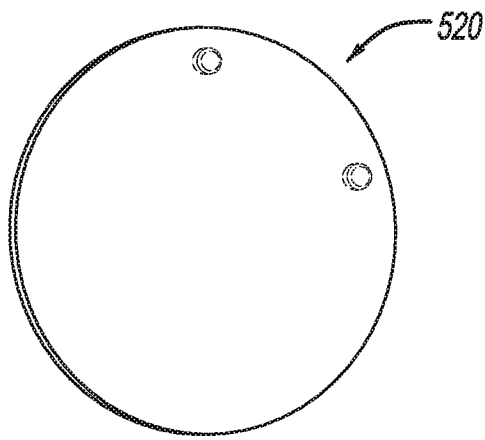
FIG-10A
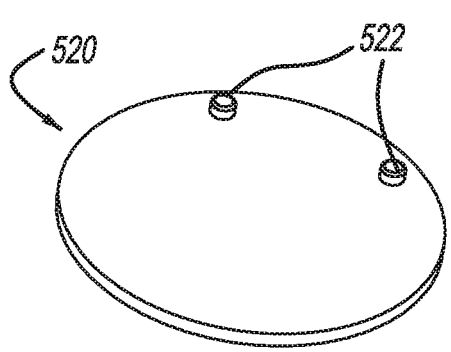
FIG-10B
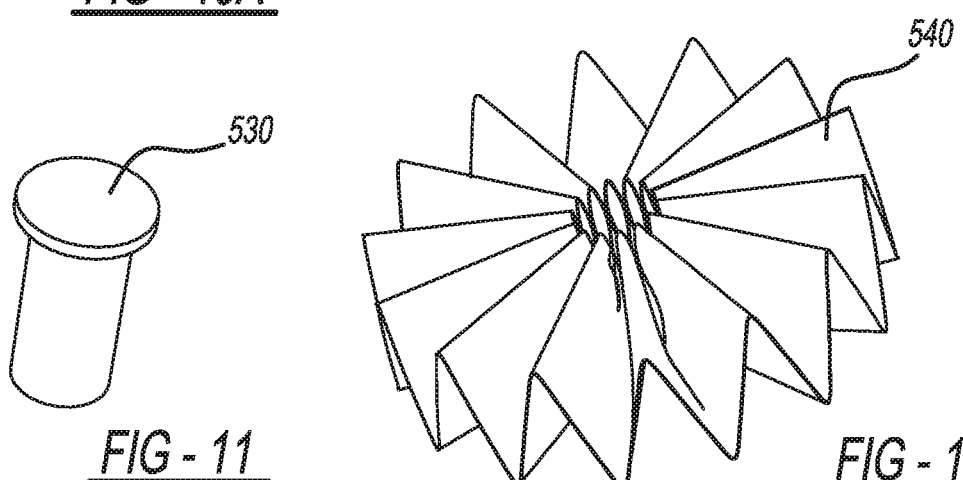
FIG-11
FIG-12

BLOOD FILTERING COMPONENT, APPARATUS, AND METHOD

CROSS-REFERENCE TO RELATED APPLICATIONS

This application is a continuation of U.S. patent application Ser. No. 15/018,800, filed Feb. 8, 2016; which is a continuation-in-part of U.S. patent application Ser. No. 13/445,837, filed Apr. 12, 2012, issued as U.S. Pat. No. 9,254,352 on Feb. 9, 2016; which claims the benefit under 35 U.S.C. § 119(e) of U.S. Provisional Application No. 62/276,817, filed Jan. 8, 2016, the disclosure of each of which is herein incorporated by reference in its entirety.

TECHNICAL FIELD

This disclosure relates generally to the field of medical devices, and more specifically, to components, devices, and methods for filtering blood or other fluids.

BACKGROUND

Autologous blood transfusion is a process that removes a patient's own blood from the body to later be re-transfused into the patient's body, as needed, during medical procedures. In developing countries, autologous blood transfusion techniques are commonly used due to the small quantities and high cost of donated blood available. These autologous blood transfusions are often performed manually. Currently, manual autologous blood transfusions involve collecting blood from an open wound or a collection surface, manually removing large blood clots, filtering the blood through gauze pads to remove smaller blood clots and biological particulates, and introducing the filtered blood into a storage bag where the blood is mixed with an anticoagulant solution and stored until the blood is needed by the patient. This process is very labor, material, and time intensive, often involving the coordination of three or more trained personnel. Furthermore, this process can suffer from sterility issues. Thus, there is a global need for improved blood transfusion devices and methods.

SUMMARY

The present disclosure provides new and useful components, devices, systems, and methods of filtering blood and other fluids. In particular, various embodiments provided herein provide components, devices, systems, and methods for performing manual autologous blood transfusions. Various embodiments provided herein overcome one or more of the shortcomings of previous manual autologous blood transfusion apparatuses and techniques.

One aspect of the disclosure is directed to a removable filter module for a blood filtering apparatus. The filter module includes a filter housing, which is formed of one or more side walls and has a partially or fully open proximal face and distal face. The filter module further includes: a filter medium disposed within the filter housing, and a body valve positioned on a distal end of the filter housing. The body valve is movable between an open and a closed configuration. In the closed configuration, the body valve seals the distal face of the filter housing. The body valve may open when a negative pressure is created within the blood filtering apparatus and may close when the pressure returns to ambient or a positive pressure.

In some embodiments, the filter module may be sized and configured to fit securely within a blood filtering apparatus and to form a liquid-tight seal with an inner wall of the blood filtering apparatus. Such a filter module may also include a sealing surface protruding from the one or more side walls of the filter housing, the sealing surface configured to compress against the inner wall of the blood filtering apparatus. The filter housing and the sealing surface may be monolithic; alternatively, the filter housing, the sealing surface, and the body valve may all be monolithic; alternatively, the filter housing, sealing surface, and body valve may each be separately formed and attached during the manufacturing process.

In some embodiments, the filter medium may be pleated. The filter housing may be cylindrical. The body valve may be formed of a flap. The filter housing may be transparent.

Another aspect of the disclosure is directed to a filter module. The filter module includes: a filter medium formed of a pleated mesh folded in a circular pattern, an elastomeric housing disposed at least partially around the filter medium, and a mechanical body valve configured to mechanically seal the filter module.

In some embodiments, the pleated mesh may form triangle-shaped facets, and the filter medium may be positioned in a circle around an inner column. The pleated mesh may have a plurality of pores sized to prevent passage of blood clots and large biological particulates through the pores while permitting passage of blood cells through the pores. The mechanical body valve may open to allow fluid to flow through the filter medium when subjected to a negative pressure and close with ambient or positive pressure. The mechanical body valve may be formed of a flap that closes when external pressure is applied on the filter module and opens when pressure within the filter module is increased.

A further aspect of the disclosure is directed to a blood filtering apparatus. The blood filtering apparatus includes a fluid uptake device having a fluid passageway, and any embodiment of the filter module described above or elsewhere herein. In various embodiments, the filter module is positionable within the passageway of the fluid uptake device.

BRIEF DESCRIPTION OF THE DRAWINGS

FIGS. 9A-9B illustrate perspective views of one embodiment of a filter housing, which forms a portion of the filter module of FIGS. 8A-8C.

FIGS. 10A-10B illustrate perspective views of one embodiment of a body valve flap, which forms a portion of the filter module of FIGS. 8A-8C.

FIG. 11 illustrates a perspective view of one embodiment of an inner column, which forms a portion of the filter module of FIGS. 8A-8C.

FIG. 12 illustrates a perspective view of one embodiment of a filter, which forms a portion of the filter module of FIGS. 8A-8C.

DETAILED DESCRIPTION

The provided figures and the following description of certain embodiments of the invention are not intended to limit the invention to these embodiments, but rather, are provided to enable any person skilled in the art to make and use this invention.

Disclosed herein are components, devices, and methods for filtering fluids; in some embodiments provided herein, the components, devices, and methods are configured for filtering blood during autologous blood transfusions.

Figure 1:
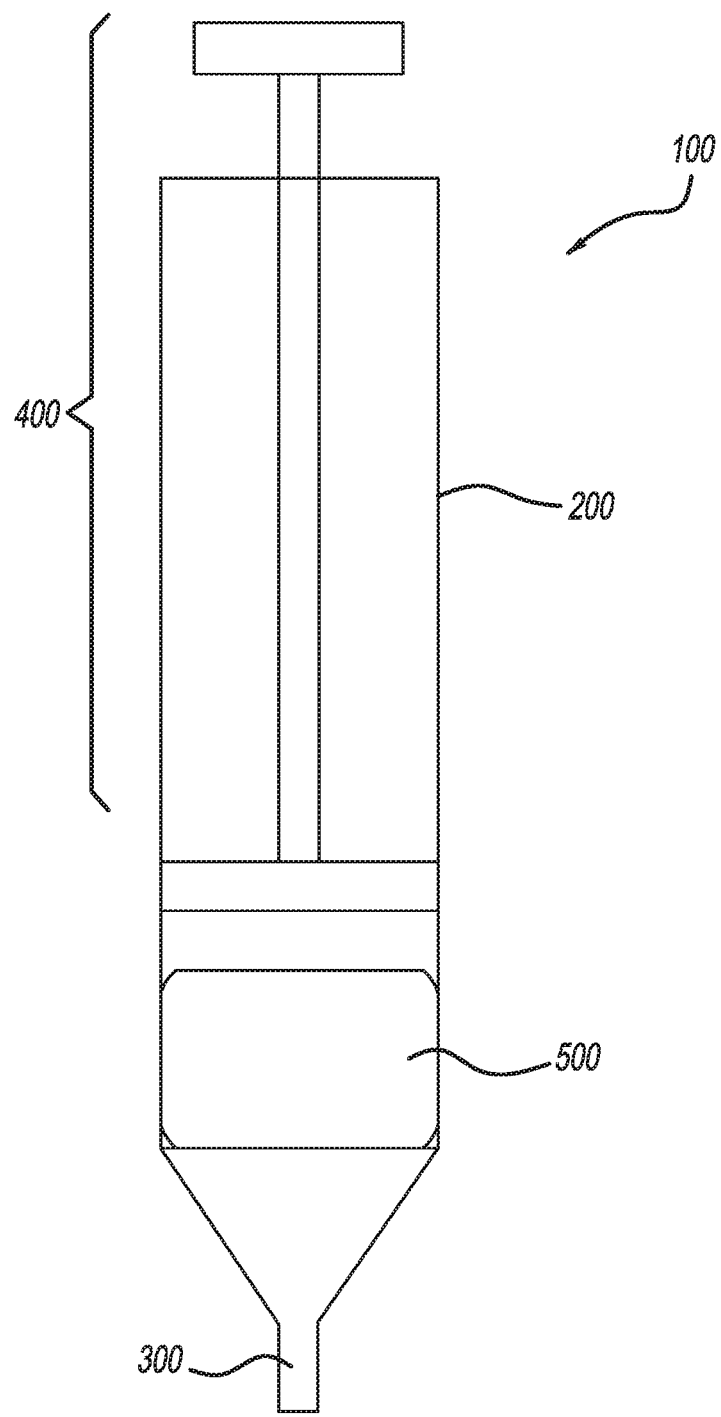
FIG. 1 illustrates a side view of one embodiment of a blood filtering apparatus.

As shown in FIG. 1, in some embodiments, an apparatus 100 for filtering blood or other fluids includes a hollow body 200, an inlet 300 fluidly coupled to the hollow body 200, a piston 400 slideably disposed within the hollow body 200, and a filter module 500 located between the inlet 300 and the piston 400. In the illustrated embodiments, the inlet 300 is at the proximal end and the piston 400 is at the distal end of the apparatus 100.

The apparatus 100 preferably functions to filter, store, and/or transport blood. For example, the apparatus 100 can be used in blood transfusions, wherein the apparatus is used to filter blood drawn from a patient or from a collection volume, such as a bowl or a floor. The apparatus preferably removes blood clots from the blood and can additionally filter foreign particulates from the blood. The apparatus is preferably passive and manually operated by a user, but can alternatively be active and driven by an electronic system.

Figure 2:
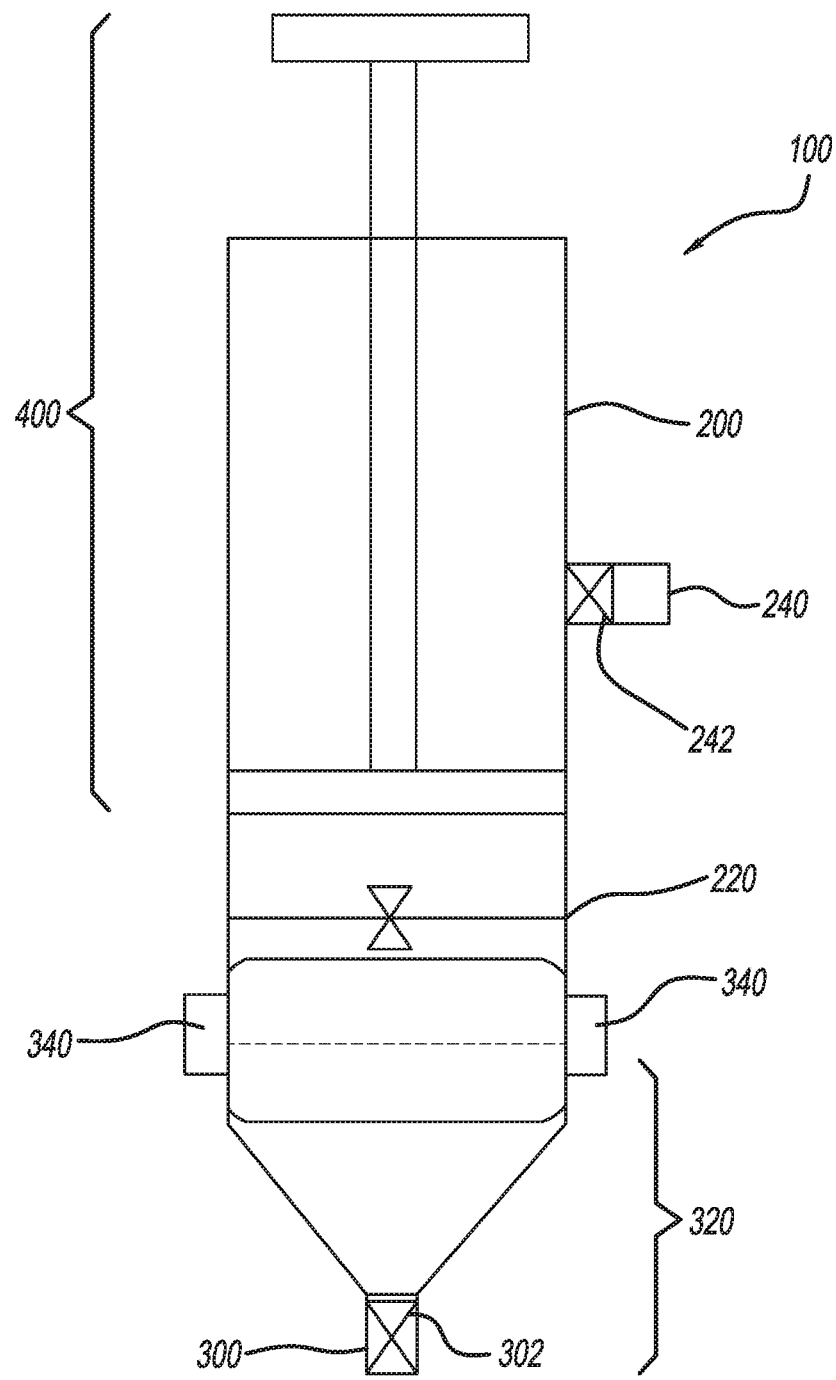
FIG. 2 illustrates a side view of one embodiment of a blood filtering apparatus.

As visible, for example, in FIG. 2, the apparatus 100 can additionally include a body valve 220 that controls fluid flow between the inlet 300 and the hollow body 200. As described in more detail below, in some embodiments, the body valve forms a portion of the filter module 500. In such embodiments, the body valve is identified as body valve 520.

Additionally or alternatively, the apparatus 100 may include an outlet 240 that allows egress of filtered fluid from the hollow body 200 without passing back through the contaminated filter.

Additionally or alternatively, the apparatus 100 may include a reservoir 320 fluidly coupling the inlet 300 to the hollow body 200. In some such embodiments, the reservoir 320 is positioned between the inlet 300 and the filter module 500. In other embodiments, the filter module 500 is positionable within the reservoir 320.

Additionally or alternatively, the apparatus 100 may include an inlet coupling mechanism 340 that removably couples the inlet 300 to the hollow body 200; in some embodiments, the inlet coupling mechanism 340 couples both the inlet 300 and reservoir 320 to the hollow body 200.

Figure 3A:
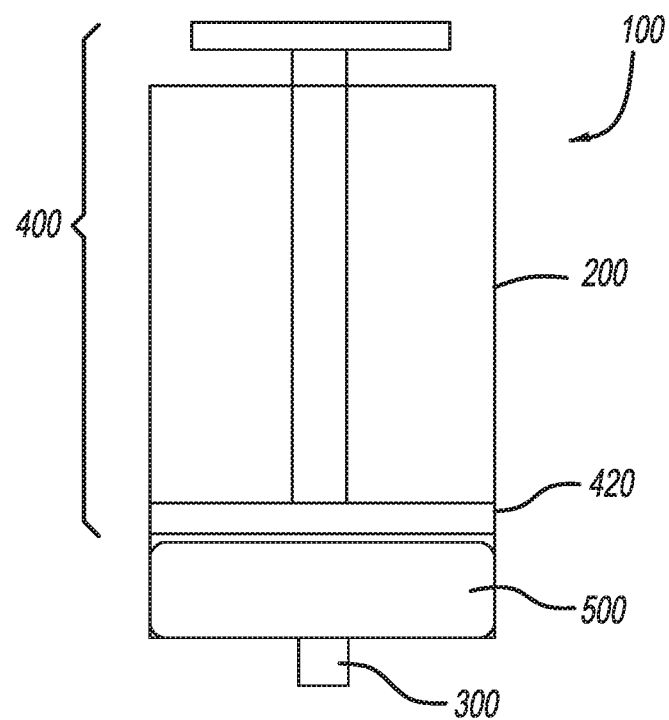
FIGS. 3A-3B illustrate a side view of one embodiment of a blood filtering apparatus moving between an empty state and a filled state, respectively.
Figure 3B:
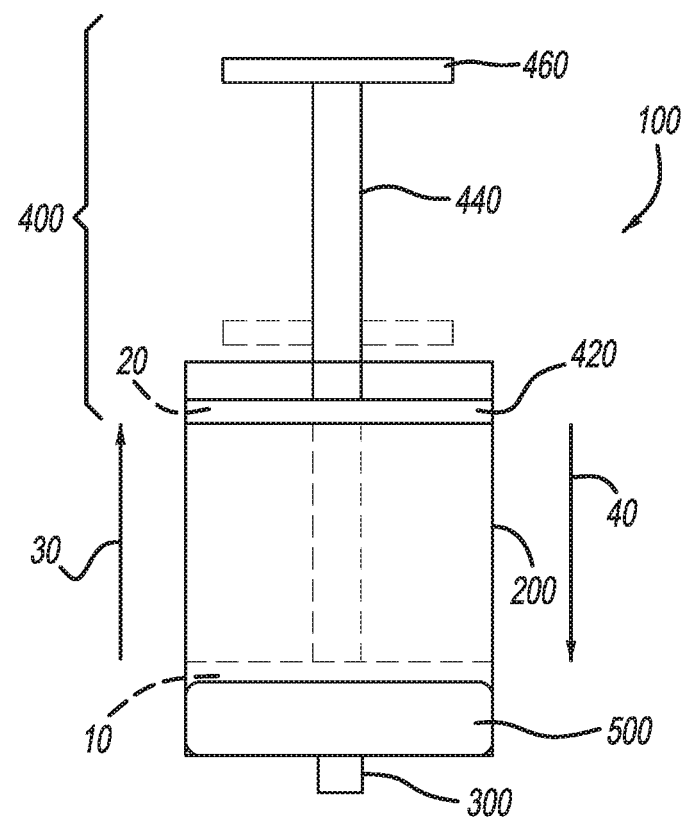

As shown in FIGS. 3A and 3B, the apparatus 100 is preferably configured to move interchangeably between an empty state (see FIG. 3A) and a filled state (see FIG. 3B) via movement of the piston 400 in a distal-moving intake stroke 30 and a proximal-moving compression stroke 40. During the intake stroke 30, the piston head 420 (i.e., the proximal end of the piston 400), moves distally from a first position 10 relatively near the inlet 300 to a second position 20 relatively far from the inlet 300. During the intake stroke 30, the piston 400 and hollow body 200 cooperatively generate a negative pressure within the hollow body 200 relative to ambient. In other words, the piston 400 applies a suction force to the hollow body interior that draws fluid through the inlet 300 and filter module 500 and into the hollow body 200. During the compression stroke 40, the piston head 420 moves from the second position 20 to the first position 10. During the compression stroke 40, the piston 400 and hollow body 200 cooperatively generate a positive pressure within the hollow body 200 relative to ambient. In other words, the piston 400 applies an expulsion force to the hollow body interior that expels fluid from the hollow body 200. The hollow body 200, piston head 420, and body valve 220/520 preferably cooperatively define a hollow body volume that expands as the piston 400 moves through the intake stroke 30, and contracts as the piston 400 moves through the compression stroke 40. The filtered fluid, more preferably filtered blood, preferably occupies the hollow body volume following an intake stroke 30.

The apparatus 100 is preferably configured to minimize clotting as the blood is drawn into the hollow body 200. The apparatus preferably minimizes clotting, at least in part, by controlling the blood flow rate into and out of the apparatus. The apparatus 100 of some embodiments allows for a blood flow rate between 0.5 L/min to 1.6 L/min. However, the apparatus 100 of other embodiments facilitates a higher or lower blood flow rate. In one embodiment, the apparatus controls the blood flow rate by controlling the maximum negative pressure (e.g., by controlling the inlet 300 to hollow body 200 cross-sectional ratio). In one embodiment, the apparatus is configured such that the maximum negative pressure does not exceed 150 mm Hg (below ambient pressure/atmospheric pressure) during the intake stroke. In another embodiment, the blood flow rate is controlled by the inlet 300 shape. In another embodiment, the blood flow rate is controlled by controlling the rate at which the piston 400 is moved through the hollow body 200 (e.g., by controlling the friction force applied by the piston head 420 against the hollow body 200 walls). However, any other suitable means or method of controlling the blood flow rate can be included.

The piston 400 of the apparatus functions to generate the pressure changes within the hollow body 200. As shown in FIG. 3B, the piston 400 of some embodiments includes a piston head 420, a shaft 440, and a handle 460, wherein the handle 460 preferably transfers an applied force to the piston head 420 through the shaft 440. The piston head 420 preferably has a substantially similar cross-section to the hollow body interior, such that the piston head 420 perimeter forms a slidable seal with the hollow body interior. The piston head 420 of some embodiments is made of a flexible material, such as rubber, but in other embodiments, it may be made of any suitable material that forms a substantially airtight seal against the hollow body interior. The shaft 440 of some embodiments has a cross-like cross-section. In other embodiments, the shaft 440 is a solid rod, hollow rod, or any other suitable form. The handle 460 of some embodiments is a T-shaped handle 460; in other embodiments, the handle 460 may be a knob, bridge, or any other suitable handle 460.

In one embodiment of the apparatus 100, the shaft 440 and the handle 460 are removably coupled to the piston head 420. This can enable the filtered blood to be stored within the apparatus instead of needing to be egressed into a blood bag for long-term storage. The pressure balance between the hollow body volume and the ambient environment preferably maintains the piston head 420 position when the shaft 440 and handle 460 are removed, but the apparatus 100 can additionally include a locking mechanism that retains the piston head 420 position. In one embodiment of the apparatus 100, the piston head 420 and shaft 440 are threaded such that rotation of the shaft 440 about its longitudinal axis removes the shaft 440 from the piston head 420. In such embodiments, the hollow body 200 interior and the piston head 420 perimeter can additionally include complimentary threading (e.g., substantially near the second position 20), wherein rotation of the shaft 440 about its longitudinal axis rotates the piston head 420 within the hollow body 200 to lock in the piston head 420 position. Further rotation, preferably in the same direction, decouples the shaft 440 from the piston head 420. In another embodiment, the piston head 420 and shaft 440 include a pin locking mechanism, wherein a portion of the shaft 440 can be depressed to release the shaft 440 from the piston head 420. Any other suitable coupling mechanism can alternatively be used to couple the piston head 420 and shaft 440.

The hollow body 200 of the apparatus 100 functions to cooperatively generate the positive and/or negative pressure with the piston 400; it also functions to hold ingressed fluid. The hollow body 200 can additionally function to retain the relative positions of other apparatus components, such as the filter module 500. The hollow body 200 preferably has a substantially constant cross-section along its length, but it can alternatively have a variable cross section. The hollow body 200 preferably has a circular cross section, but it can alternatively have an ovular, rectangular, polygonal, or any other suitable cross section. In one embodiment of the apparatus, the hollow body 200 is a hollow cylinder. The hollow body 200 is preferably substantially rigid, and is preferably made of biocompatible materials. The hollow body 200 can additionally include a coating on the hollow body interior, wherein the coating is preferably a biocompatible coating. In some embodiments, the coating is an anticoagulant coating.

The hollow body 200 can additionally include a piston retention element, which functions to prevent complete piston removal from the hollow body. The position of the piston retention element within the hollow body can additionally function to define the second position 20. The piston retention element is preferably located along the hollow body 200 length distal to the first position 10. The piston retention element is preferably operable between a retention mode, wherein the piston retention element retains the piston head within the hollow body, and a release mode wherein the piston retention element allows complete piston head retraction from the hollow body (e.g., to allow for disassembly and sterilization). In one variation, the apparatus 100 includes one or more through-holes and one or more corresponding pins as the piston retention element, wherein the pins extend through the through-holes to block piston head retraction past the pins. The pins can be removably coupled to the through-holes to allow apparatus disassembly. However, any other suitable piston retention element configuration can be used.

Additionally or alternatively, the hollow body 200 may include a piston arrest distal the inlet 300, wherein the piston arrest preferably defines the maximum distance that the piston 400 can travel away from the inlet 300.

The hollow body 200 may additionally or alternatively include a filter retention area including a series of grooves in which the filter module 500 sits. The filter retention area is preferably located on the proximal end of the hollow body 200 in, adjacent to, or near the reservoir 320, but it can alternatively be located in any suitable position.

The inlet 300 of the apparatus 100 functions to facilitate blood ingress into the hollow body 200. The inlet 300 can additionally filter out large blood clots. In various embodiments, the inlet 300 is operatively connected to a proximal end of the hollow body 200. Preferably, the inlet 300 is concentric with the hollow body 200, but it can alternatively be coupled to any suitable portion of the hollow body 200. The inlet 300 is preferably a nozzle defining a straight channel; however, the nozzle can alternatively define a tapering channel, a swirl channel, or any other suitable channel. The nozzle preferably has a flat tip, but can alternatively have an angled tip, a threaded tip, a barbed tip, or any other suitable tip. Alternatively, the inlet 300 can be any other suitable fluid inlet. The inlet 300 can additionally be configured to minimize clotting during blood ingress. In one example of the apparatus 100, the ratio between the cross-sectional areas of the inlet 300 and the hollow body 200 is configured such that the maximum negative pressure within the hollow body 200 does not exceed 150 millimeters of mercury during the intake stroke. The inlet 300 is preferably removably coupled to the hollow body 200, for example, being removably coupled via an inlet coupling mechanism 340. In other embodiments, the inlet 300 is formed as a singular piece with the hollow body 200. The inlet 300 can additionally include features for component attachment, such as barbs or threading. Components that can be attached to the inlet 300 include a needle, an IV tube, a blood bag, or any other suitable component.

Figure 4:
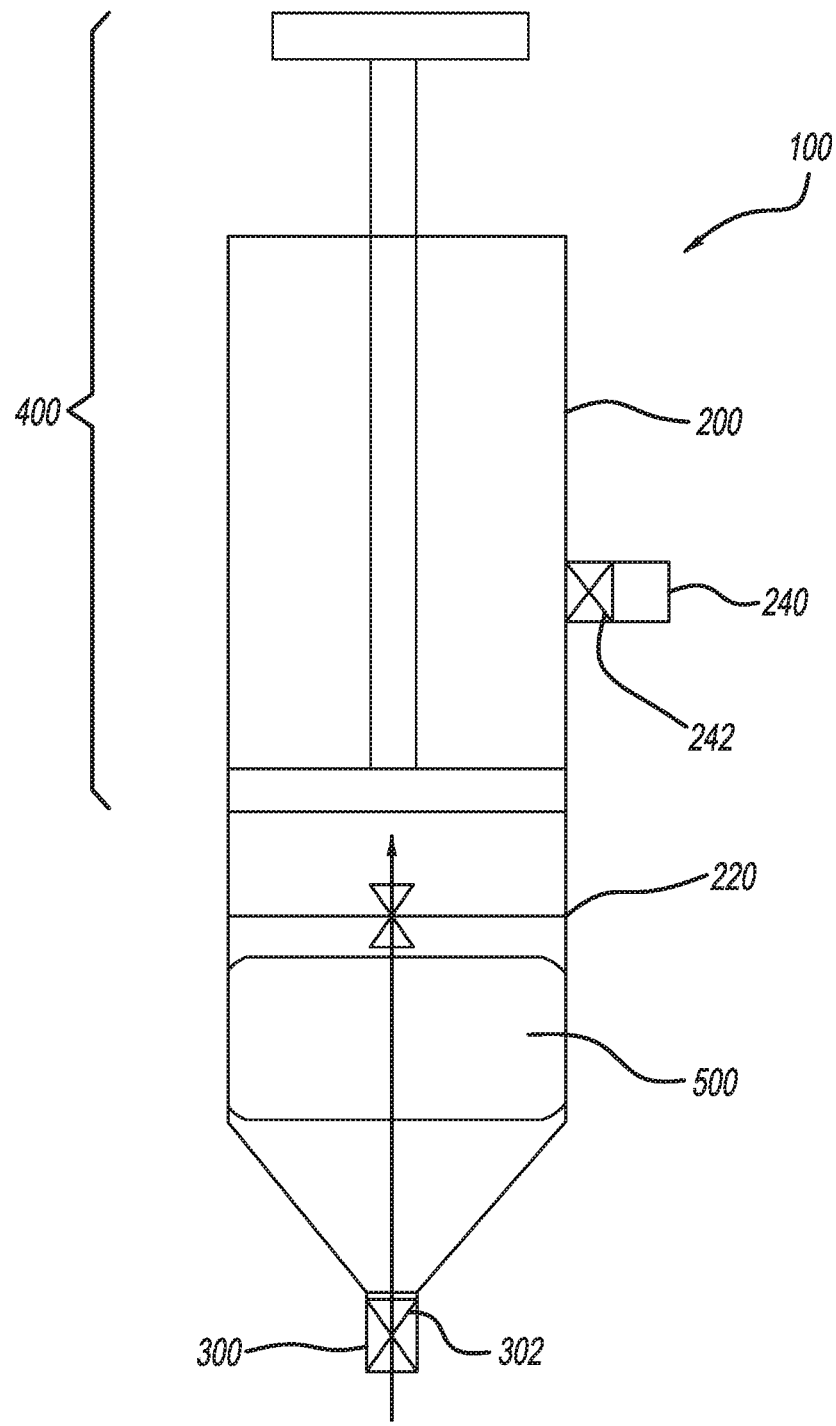
FIG. 4 illustrates a side view of one embodiment of a blood filtering apparatus.

As shown, for example, in FIG. 4, the inlet 300 can additionally include an inlet valve 302 positioned in the channel of the inlet 300 or between the inlet 300 and the filter module 500. The inlet valve 302 is preferably in an open position when the hollow body volume is under negative pressure and in a closed position when the hollow body volume is under positive pressure and/or at ambient pressure (e.g., atmospheric pressure). The inlet valve 302 is preferably a passive, one-way valve, but can alternatively be an active valve, a multi-way valve, or any other suitable valve. Example inlet valves 302 include a duckbill valve, a switch valve, a ball valve, or any other suitable valve.

As shown, for example, in FIG. 4, the apparatus can additionally include an outlet 240 that functions to egress blood from the hollow body 200. The outlet 240 preferably provides a second fluid path for fluid egress that is different from the path of fluid ingress/fluid filtration. The outlet 240 preferably permits fluid egress from the hollow body 200 during the compression stroke, when positive pressure is applied to the hollow body interior. The outlet 240 is preferably located along the length of the hollow body 200. In some embodiments, the outlet 240 is positioned between the filter module 500 and the piston head 420 in the first position 10; in other embodiments, the outlet 240 is positioned between the filter module 500 and the piston head 420 in the second position 20. Thus, the filtered fluid does not need to flow through the contaminated fluid to egress from the hollow body 200. The outlet 240 preferably includes an outlet barb or threading to which a blood bag, tubing, or any other suitable transfusion mechanism can be coupled. The ratio between the cross-sectional area of the outlet 240 and the hollow body 200 is preferably configured to limit the maximum positive pressure to a suitable pressure, for example, 150 millimeters of mercury.

Figures 5A, 5B:
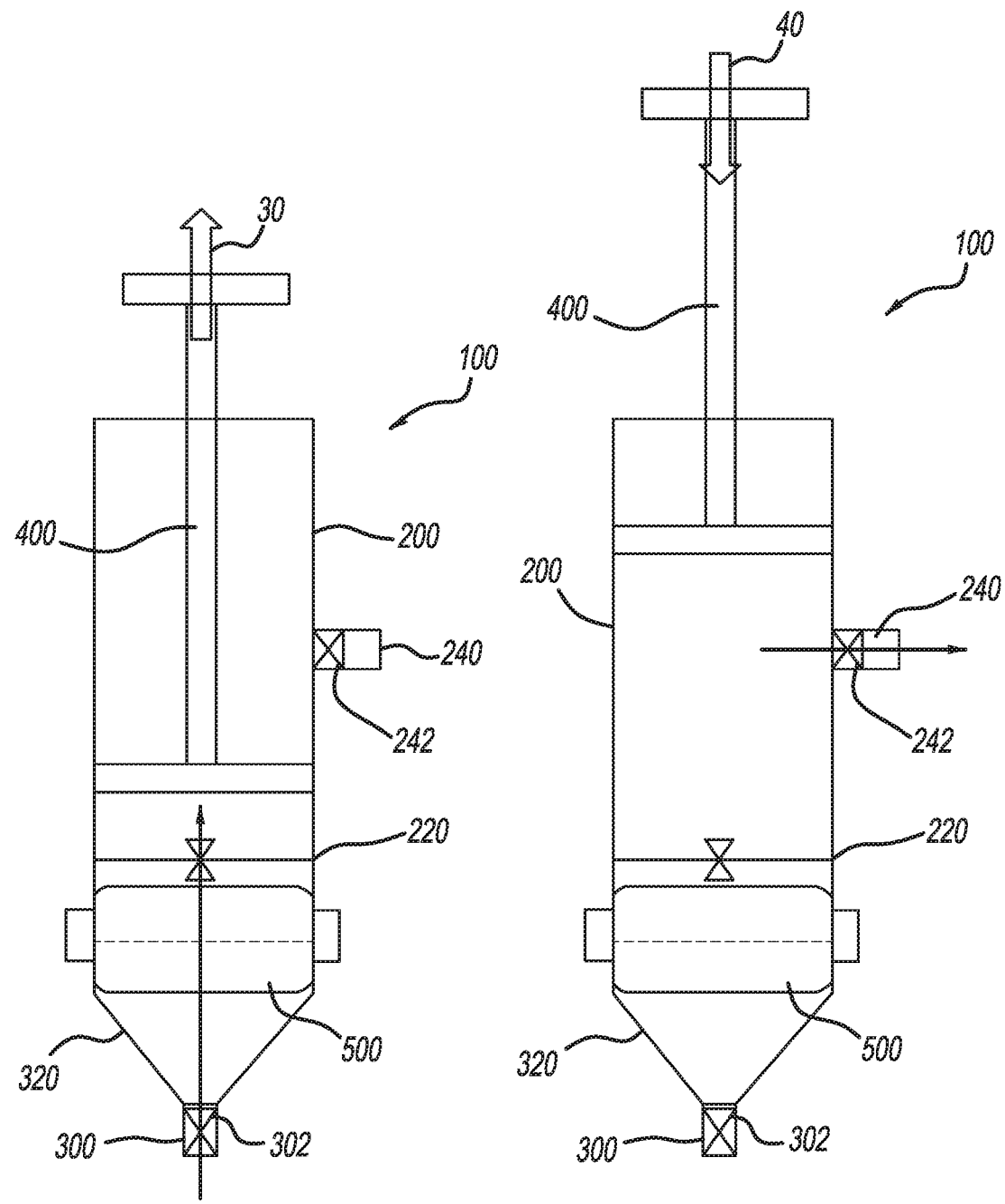
FIGS. 5A-5B illustrate a side view of one embodiment of a blood filtering apparatus moving through an intake stroke and a compression stroke, respectively.

The outlet 240 can additionally include an outlet valve 242 between the outlet 240 and the body 200. The outlet valve 242 is preferably a passive, one-way valve, but can alternatively be an active valve, a multi-way valve, or any other suitable valve. Example outlet valves 242 include a duckbill valve, a switch valve, a ball valve, or any other suitable valve. In one embodiment of the apparatus 100, as shown in FIG. 5A, the outlet valve 242 is preferably in a closed position when the hollow body volume is under negative pressure and/or is at ambient pressure (e.g., atmospheric pressure), and as shown in FIG. 5B, is in an open position when the hollow body volume is under positive pressure.

In another embodiment of the apparatus, the outlet valve 242 is in an open position when the hollow body volume is under negative pressure, in an open position when the hollow body volume is under positive pressure, and in a closed position when the hollow body volume pressure is substantially equal to the atmospheric pressure. In this embodiment, a blood bag containing an anticoagulant solution can be coupled to the outlet 240 prior to the intake stroke. When the piston 400 is moved through the intake stroke, blood and anticoagulant are simultaneously drawn into the hollow body volume through the inlet 300 and outlet 240, respectively, wherein the blood mixes with the anticoagulant within the hollow body volume. Translation of the piston 400 through the compression stroke then pushes the anticoagulant-blood mixture into the coupled blood transfusion device (e.g., blood bag). In this embodiment, the outlet 240 can additionally include a microfilter that functions to filter microorganisms and/or particulates from the anticoagulant solution prior to ingress into the hollow body volume; the microfilter is preferably removed prior to solution egress from the hollow body 200. In some embodiments, coupling a blood transfusion device (e.g., a blood bag) to the outlet 240 can switch the outlet 240 from maintaining a closed position during the intake stroke to maintaining an open position during the intake stroke.

Additionally or alternatively, the apparatus 100 can include a volume of anticoagulant solution, for example, within the hollow body 200, wherein blood can mix with the anticoagulant solution upon ingress into the hollow body volume. The anticoagulant solution can include one or more antithrombotics, such as heparin or coumarin compounds, one or more thrombolytics, such as streptokinase or urokinase, and/or one or more antithrombocytics. The anticoagulant volume within the hollow body 200 is preferably less than the maximum hollow body volume achieved when the piston head 420 is in the second position 20. In some embodiments, the anticoagulant volume is less than half the maximum hollow body volume. Alternatively, any suitable volume of anticoagulant solution can be included, wherein the anticoagulant volume is preferably determined based on the concentration of the anticoagulant solution.

Figure 6:
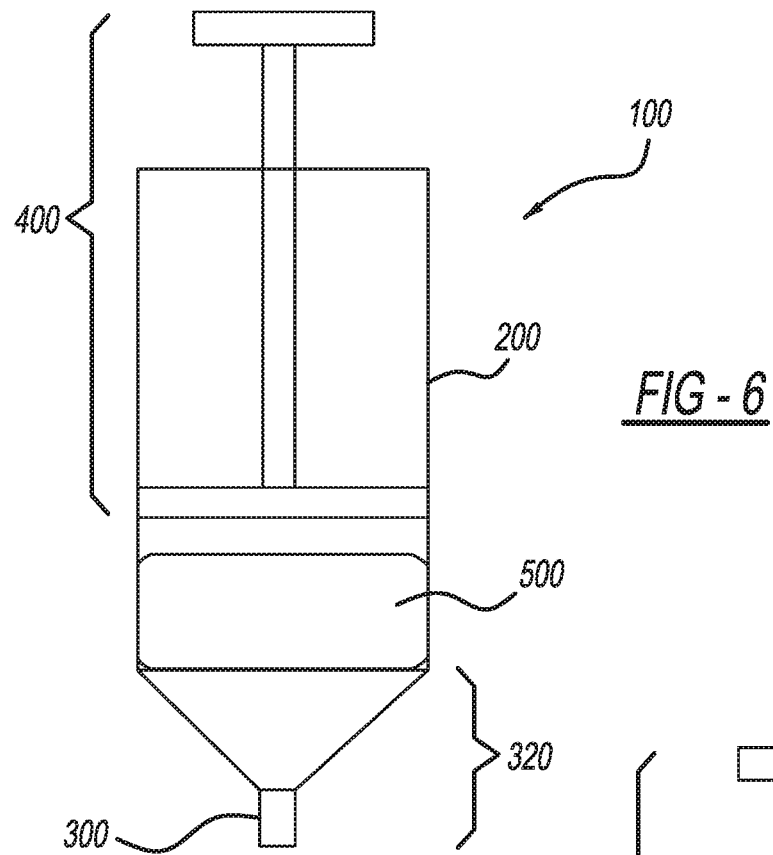
FIG. 6 illustrates a side view of one embodiment of a blood filtering apparatus.
Figure 7:
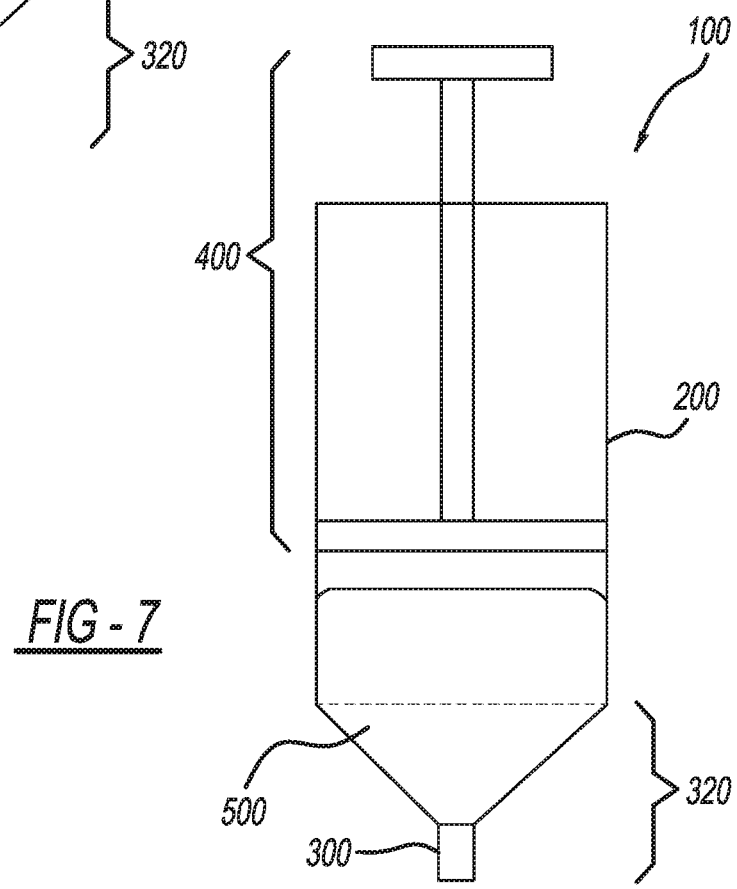
FIG. 7 illustrates a side view of one embodiment of a blood filtering apparatus.

As shown, for example, in FIGS. 5A-7, the apparatus can additionally include a reservoir 320 that couples the inlet 300 to the hollow body 200. The reservoir 320 is preferably substantially hollow, and defines a reservoir volume. The reservoir configuration preferably minimizes blood clot formation, and preferably promotes laminar flow and/or minimizes turbulent flow between the inlet 300 and the hollow body 200. For example, in various embodiments, the reservoir 320 provides a smooth transition between the inlet 300 and the hollow body 200. The reservoir 320 can additionally provide a region for liquid and clotted blood to enter the apparatus 100 with sufficient volume for the liquid blood to separate from the solid clots and enter the filter. The reservoir 320 then acts as a storage area for the clots that cannot pass through the filter. The reservoir 320 of some embodiments, such as the embodiment of FIG. 6, is unoccupied by other apparatus components. In such embodiments, the filter module 500 is positioned distal to the reservoir 320. The reservoir 320 of other embodiments, such as the embodiment of FIG. 7, is partially or wholly occupied by the filter module 500 (e.g., when the filter module 500 is conical).

In one embodiment of the apparatus 100, the reservoir 320 is conical, the inlet 300 is located at the tip of the conical reservoir 320, and the hollow body 200 couples to the base of the conical reservoir 320. The reservoir 320 can be a parabolic cone, an elliptical cone, a frustum, a cylinder, or any other suitable shape, wherein the inlet 300 is preferably located at the reservoir apex, concentric with the reservoir central axis, but can alternatively be located in any other suitable position. The reservoir 320 and inlet 300 are preferably manufactured as a singular piece, but can alternatively be manufactured as separate pieces.

Returning, for example, to FIG. 2, the apparatus can additionally include an inlet coupling mechanism 340 that removably couples the inlet 300 to the hollow body 200. More preferably, the inlet coupling mechanism 340 removably couples the reservoir 320 and inlet 302 to the hollow body 200. The inlet coupling mechanism 340 preferably enables the apparatus to be movable between an open and closed configuration. In the open configuration, the reservoir 320 is at least partially decoupled from the hollow body 200 such that the filter module 500 can be accessed. In some embodiments, the filter module 500 can be removed from the apparatus when the apparatus 100 is in the open configuration. In the open configuration of the inlet coupling mechanism 340, the body valve 220/520 preferably seals the hollow body volume to prevent contamination. In the closed configuration, the reservoir 320 perimeter preferably forms a fluid impermeable seal with the hollow body 200 perimeter. The reservoir-hollow body junction can additionally include an O-ring or gasket to facilitate a better fluid seal. By allowing the apparatus 100 to be opened, the inlet coupling mechanism 340 can allow for apparatus disassembly, which can facilitate apparatus component sterilization (e.g., autoclaving), filter replacement, and apparatus reuse.

In one embodiment of the apparatus, the inlet coupling mechanism 340 includes at least two complimentary connecting mechanisms. The connecting mechanisms may be evenly distributed about the reservoir 320 and hollow body 200 perimeters. In another embodiment of the apparatus, the inlet coupling mechanism 340 includes a hinge rotatably connecting the hollow body 200 and reservoir 320 and a connecting mechanism, wherein the connecting mechanism and hinge cooperatively seal the reservoir 320 against the hollow body 200 when the connecting mechanism is engaged. The connecting mechanism can include one or more clips, screws, adhesives, latches, clips, bayonet locking components, spring-force mechanisms (e.g., a rubber band that is stretched between the reservoir 320 and the hollow body 200 distal the reservoir 320), complementary threading, or any other suitable coupling mechanism.

The filter module 500 of the apparatus 100 functions to separate blood clots from the blood volume, wherein blood is preferably drawn across the filter module 500 before entering the hollow body volume during the intake stroke. In some embodiments, the filter module 500 is arranged within the hollow body 200 and preferably extends across an entire cross section of the hollow body 200. The filter module 500 can alternatively be partially or wholly located within the reservoir 320. The filter module 500 can have any suitable shape. The filter module 500 of some embodiments is cylindrical (e.g., disc-shaped) with a diameter substantially equivalent to the hollow body interior diameter. In other embodiments, the filter is conical; in one embodiment, the conical filter substantially fills the volume of the reservoir 320. The filter module 500 is preferably assembled such that it is concentric with the hollow body 200, but it can be assembled in any suitable position relative to the hollow body 200. The filter module 500 of some embodiments is coupled to the hollow body 200 (e.g., within a filter module slot). The filter module 500 of other embodiments is coupled to the reservoir 320 (e.g., within a filter module slot). In some embodiments in which the reservoir 320 is removably attached to the hollow body 200, removal of the reservoir 320 simultaneously removes the filter module 500 as well. In other embodiments, removal of the reservoir 320 exposes the filter module 500 for easy removal from the hollow body 200.

The filter module 500 preferably includes at least one porous filter. The pore size of the filter is preferably large enough to allow blood cells (e.g., erythrocytes) to pass through the filter, and is preferably small enough to filter out clots. The pore size is preferably no more than 170 μm (diameter), and in some embodiments, the pore size is between 40 μm to 170 μm, but in other embodiments, the pore size can alternatively be larger or smaller. The pore size can be selected based upon the application (e.g., dependent on the species from which the blood originated). The pore size of some embodiments is substantially uniform throughout the filter, but in other embodiments, it uniformly or non-uniformly varies throughout the filter. The filter of some embodiments has 50% porosity, but in other embodiments, the filter can have any suitable porosity between 0% and 100%. The filter is preferably made of a biocompatible material, such as nylon or polyester, but it can alternatively and/or additionally be made of cloth, paper, ceramic, coated polymers, coated metals, or any other suitable material. The filter of some embodiments is a substantially uniform, singular piece. In other embodiments, the filter is made of multiple pleated filters extending radially from a central axis. The filter is preferably a disc or block, but can alternatively be a membrane. The filter module 500 can include any suitable number of filters with any suitable pore size, wherein the filters with larger pore sizes are preferably disposed proximal to the filters with smaller pore sizes. In apparatus variations with multiple filters, the filters are preferably adjoined (e.g., touching the adjacent filter), but can alternatively be separated from the adjacent filter by a given distance.

Figure 8A:
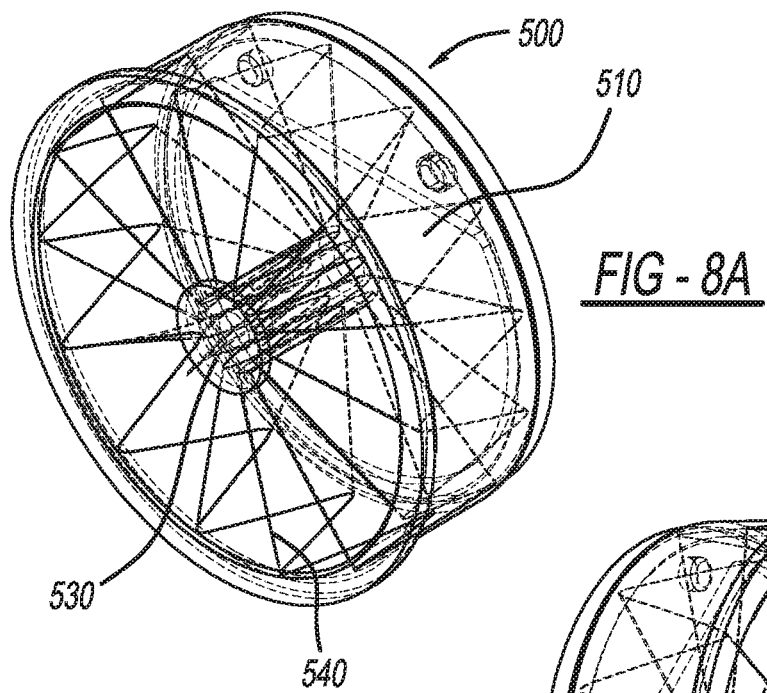
FIGS. 8A-8C illustrate perspective views of one embodiment of a filter module for use in various embodiments of the blood filtering apparatus.
Figure 8B:
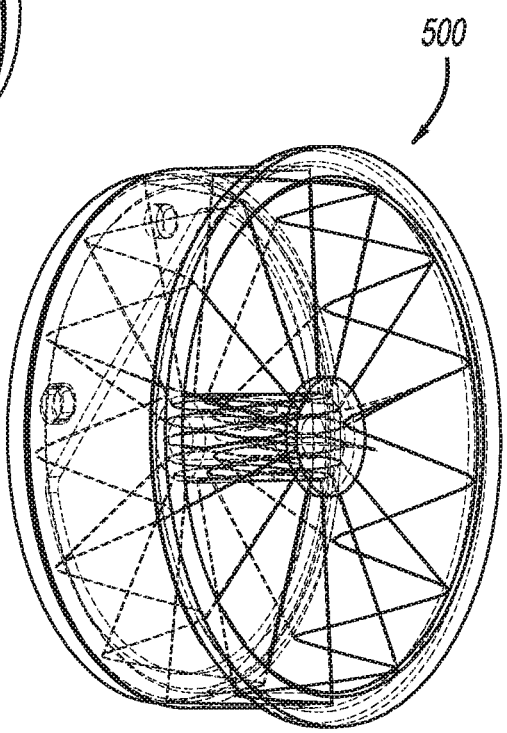
Figure 8C:
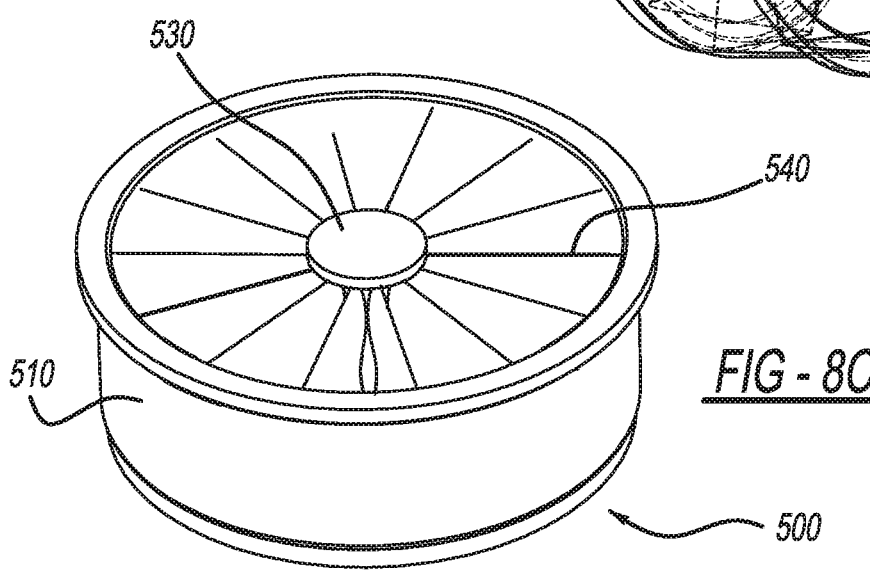
Figure 13:
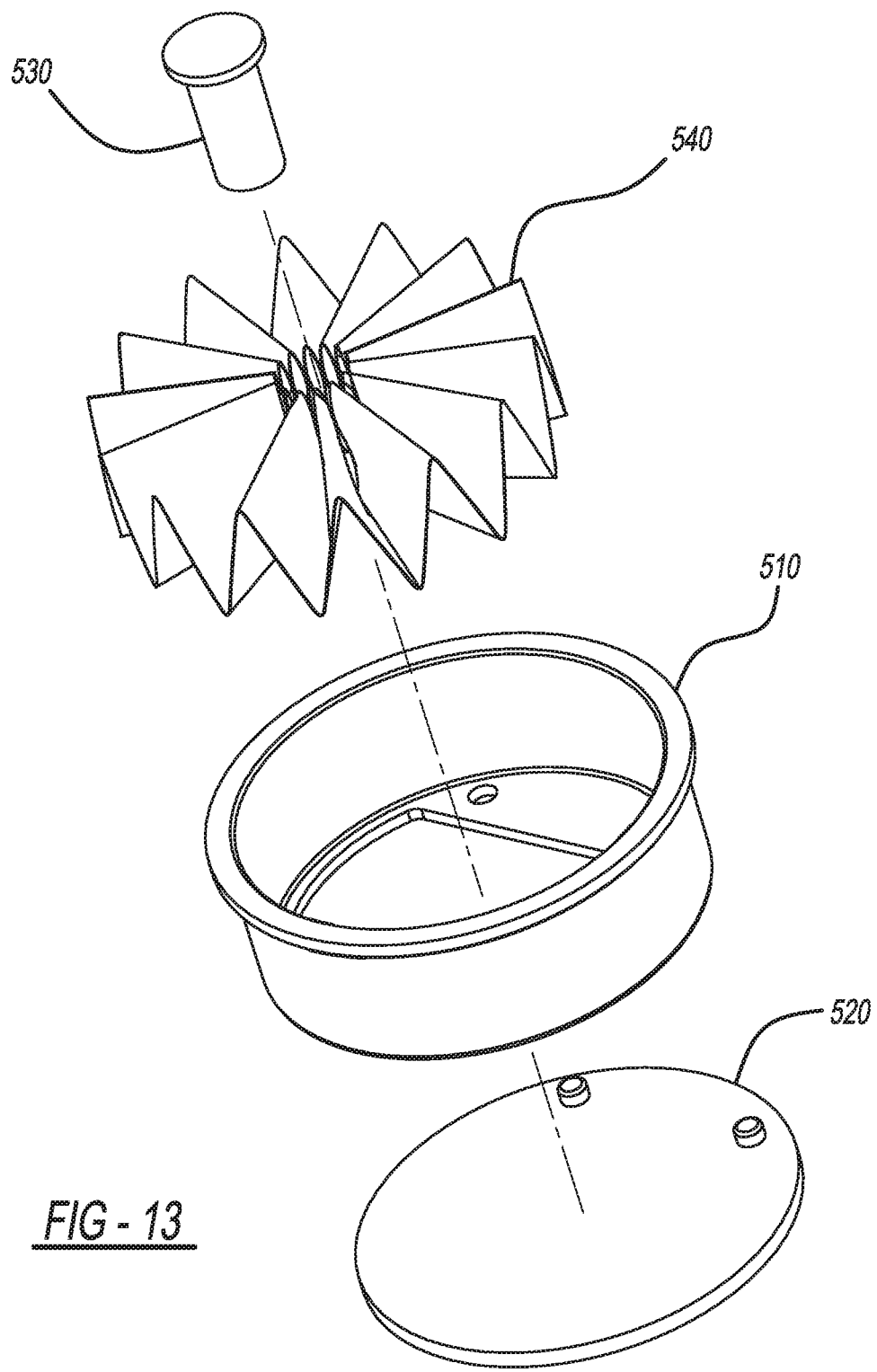
FIG. 13 illustrates an exploded view of the filter module embodiment of FIGS. 8A-8C.

One embodiment of a filter module 500 is shown in FIGS. 8A-8C. The illustrated filter module may form a portion of an autologous blood transfusion device. For example, the filter module 500 may form a portion of any embodiment of the apparatus 100 described elsewhere herein. In various embodiments, the filter module 500 includes both a filter and a body valve, and the filter module is configured to both filter fluid and control the flow of fluid through the filter. Such embodiments of the filter module are formed of a filter mesh 540 (also referred to as a filter medium), a filter housing 510, and a body valve flap 520. The embodiments may additionally include an inner column 530. Examples of some individual components of the filter module are shown in FIGS. 9A-12. In particular, FIGS. 9A-9B provide one embodiment of a filter housing 510, FIGS. 10A-10B provide one embodiment of a body valve flap 520, FIG. 11 provides one embodiment of an inner column 530, and FIG. 12 provides one embodiment of a filter mesh 540.

In the filter module embodiment of FIGS. 8A-8C, the filter mesh 540 is disposed in the filter housing 510. The filter housing 510 is formed of a side wall and has partially or fully open proximal and distal faces. In some embodiments, the filter housing 510 is formed of a cylindrical side wall. In some embodiments, the filter housing includes one or more protrusions or other structural features on the side wall(s), for example, to facilitate a fluid-tight seal between the filter module and the adjacent portions of the blood filtering apparatus. For example, as shown in FIGS. 9A-9B, in some embodiments, the filter housing 510 includes a side wall 512, one or more an outwardly extending protrusions 514 at a first end, and one or more inwardly extending protrusions 516 at a second end. In some embodiments, the outwardly extending protrusion 514 acts as a sealing surface, compressing against the inner perimeter of the component in which the filter module 500 is positioned (e.g., the hollow body 200 or the reservoir 320) so as to create a seal between the filter module 500 and the inner perimeter of the surrounding component. Such a seal prevents fluid from bypassing the filter medium. In some embodiments, the inwardly extending protrusion 516 acts as a sealing surface, creating a seal between the filter housing 510 and the body valve flap 520. The sealing surface 516 and body valve flap 520 together create a temporary seal across a face of the filter module 500 so as to prevent fluid from exiting the filter module in the wrong direction.

In various embodiments, a body valve flap 520 is positioned across the distal or proximal face of the filter housing 510. In some embodiments, the body valve flap 520 and filter housing 510 include interlocking features, such as the mating holes 518 and protrusions 522 shown in FIGS. 9A-10B. Additionally or alternatively, an adhesive may be used to secure the body valve flap 520 to the filter housing 510.

In some embodiments, the body valve flap and/or one or more sealing surfaces (e.g., outwardly extending protrusions 514 and inwardly extending protrusions 516) are integrally/monolithically formed with the side wall(s) 512 of the filter housing 510. In some embodiments, the sealing surface(s) 514, 516 and/or body valve flap 520 are separately formed and attachable to the filter housing. In some embodiments, the body valve flap 520 is mechanically or chemically bonded to a portion of the side wall 512 of the filter housing 510 or the sealing surface 516.

The sealing surfaces of some embodiments are made of a thermoplastic elastomer, such as, for example, GLS Versaflex CL2242. The sealing surfaces of other embodiments are made from any number of common elastomers known to those skilled in the art. Exemplary materials include, but are not limited to, Buna-N, EPDM, Fluorosilicone, Neoprene, Polyurethane, Silicone, and Viton. As shown, for example, in FIGS. 14A-14B, in some embodiments, the entire filter module 500, or the entire filter module 500 except for the filter mesh 540, is made of a transparent material to allow for visual inspection for blood clots.

The filter 540 of various embodiments of the filter module 500 is formed of a mesh configured to remove any biological particulates not suitable for autologous transfusion. In the illustrated embodiments, there are two layers of filter mesh. The first layer has a coarse pore size, for example, with pores in the range of 800 microns to 1 mm. The second layer has a finer pore size, for example, in the range of 100-170 microns; such a size allows blood cells to pass through the filter mesh while preventing the passage of larger components, such as blood clots and bone particulates. In other embodiments, one layer of mesh is provided, while in other embodiments, three or more layers of mesh are included within the filter module. In various embodiments having at least two filters with different pore sizes, the fine filter preferably has a pore size of less than 170 µm, and more preferably between 40 µm and 170 µm. The coarse filter preferably has a pore size larger than the fine filter, and is preferably located closer to the inlet 300 than the fine filter is, thereby acting as a pre-filter. By removing larger clots before they can engage with the smaller pores of the fine filter, the coarse filter can increase the longevity of the original filter by preventing the fine filter from becoming clogged with the larger clots. The coarse filter of some embodiments has a pore size no more than 170 µm (e.g., 80 µm, 100 µm, 150 µm, etc.), but in other embodiments, the coarse filter has a pore size that is larger (e.g., 200 µm, 600 µm, 0.1 mm, etc.). The coarse filter of some embodiments is adjoined to the fine filter; it can alternatively be retained a distance away from the fine filter. In one embodiment, both the coarse filter and the fine filter are discs of substantially the same diameter. In another embodiment, the coarse filter is conical while the fine filter is substantially frustoconical, wherein the coarse filter base has a diameter substantially equal to the diameter of the smaller base of the fine filter, and the combined filter module 500 fits within the interior volume of the reservoir 320.

In one embodiment, the filter module 500 is in the form of a filter cartridge, which can be removably coupled to the hollow body 200 or the reservoir 320. In some embodiments, the hollow body 200 includes a filter cartridge slot that the filter module 500 is configured to fit within. The filter module 500 can be placed in or removed from the filter cartridge slot. The filter module 500 and filter cartridge slot preferably form a seal therebetween, such that blood flows substantially through the filter, and does not leak through the perimeter of the filter module 500. The apparatus can additionally include an O-ring between the filter module 500 and filter cartridge slot to facilitate a sufficient seal.

During assembly of some embodiments, the filter mesh 540 is placed or formed within the filter housing 510. In some embodiments, for example, in some embodiments having a cylindrical filter module 500, the filter mesh 540 is pleated in alternating folds and wrapped in a circle around an inner column 530. The pleats of some embodiments form triangle-shaped facets. In some such embodiments, each pleat of the filter mesh 540 extends the entire height or a substantial height of the cylindrical side wall 512 with the folds at or near the top and bottom (i.e., proximal and distal faces) of the side wall 512. The side wall 512 of the filter housing 510 and the inner column 530 stabilize the filter mesh 540 in place and help it maintain its shape. The inner column 530 may be monolithically formed with the filter housing 510, or the inner column 530 may be securely adhered or otherwise attached to the filter housing 510. In other embodiments, the filter module 500 may be sized and shaped to fit within a non-cylindrical, tubular portion of a blood filtering apparatus 100. In such embodiments, the filter housing 510 may have a different polygonal shape, such as, but not limited to, rectangular. In such embodiments, the pleated filter mesh 540 may have a matching or otherwise complementary shape. For example, in some embodiments, both the filter housing 510 and the pleated filter mesh 540 are rectangular. In such embodiments, the inner column 530 may not be present. In various embodiments, the filter mesh 540 is oriented such that the open faces of each fold are directed towards the open faces (i.e., the distal and proximal faces) of the filter housing 510.

A bonding method may be used to secure the filter mesh 540 to the filter housing 510. In some embodiments, Loctite 5240 UV cure adhesive is used to attach the filter to the housing. In other embodiments, other suitable biocompatible adhesives (e.g., UV cure, air dry, vulcanizing, two-part) are used alone or in combination. Additionally, in some embodiments, the filter housing 510 is overmolded to the filter 540, embedding a portion of the filter mesh 540 within the filter housing 510 and/or the inner column 530 (if present).

The filter mesh 540 is made of a material that is compatible with blood and likely to minimize damage to blood as the blood passes through the filter mesh. In certain embodiments, the filter mesh 540 is pleated and presented in a circular shape, allowing for greater flow through the filter than a flat disc. This maximizes the volume flow and reduces the stress on the red blood cells to prevent cellular rupture. If the pressure on the cells rises above 150 mmHg of pressure, the likelihood of damage increases significantly. Alternately, the filter mesh 540 may be presented in other configurations such as flat, curved, or conical shapes. The housing 510 of some embodiments is made of an elastomer to enable a tight seal between the blood filtering apparatus 100 and the filter module 500. The inner column 530 of some embodiments is made of the same or different elastomer as the filter housing 510. In other embodiments, the inner column 530 is not elastomeric. In some embodiments, both the filter housing 510 and the inner column 530 (if present) are bonded to the filter mesh 540 to prevent fluid from bypassing the mesh 540.

Figure 14A:
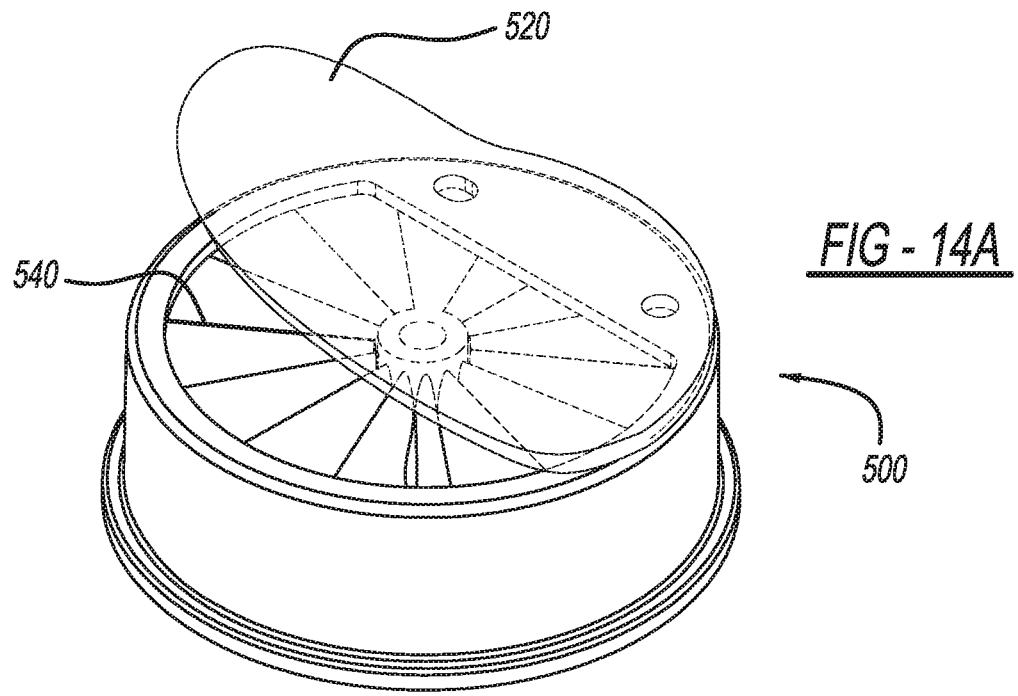
FIG. 14A illustrates a perspective view of one embodiment of a filter module having a body valve in an open position.
Figure 14B:
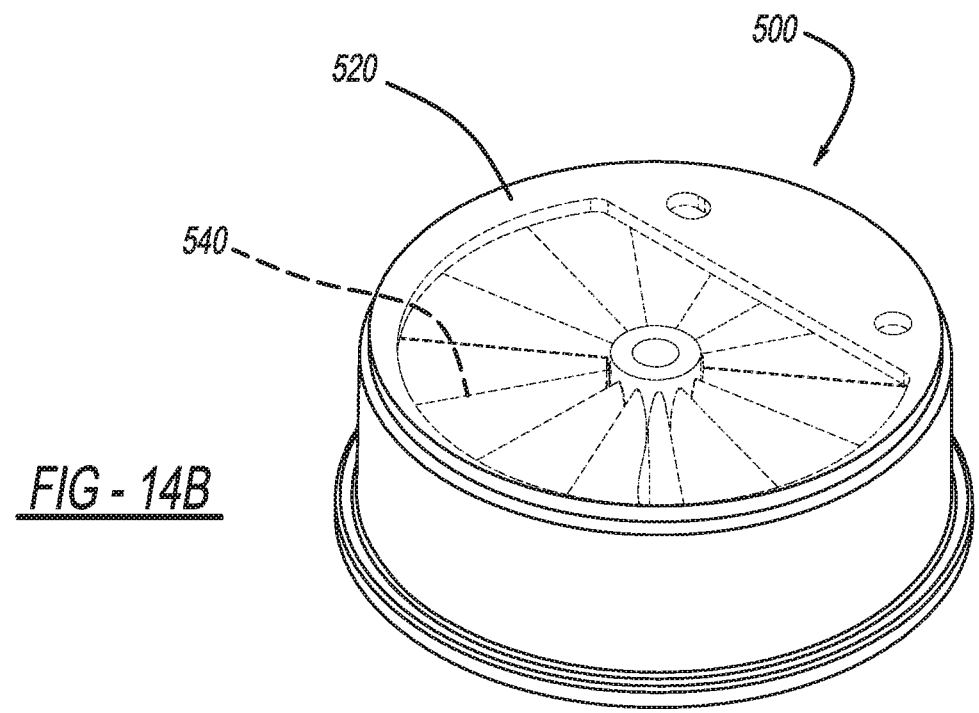
FIG. 14B illustrates a perspective view of the filter module embodiment of FIG. 14A, with the body valve in a closed position.

In some embodiments, on one of the open faces of the filter housing 510 (i.e., on the proximal or distal end), the body valve flap 520 covers the entire face and is partly attached to the filter housing 510. In a preferred embodiment, the body valve flap 520 covers the distal face of the filter housing 510. As described above, the body valve flap 520 may be mechanically and/or chemically bonded to a portion of the filter housing 510. The flap 520, which is flexible, opens by bending along a joint such that the unattached portion of the flap 520 moves outward away from the filter housing 510. An example of an open configuration is shown in FIG. 14A. Opening of the valve flap 520 allows blood to flow through the filter mesh 540 and pass through to another chamber of a blood filtering apparatus 100 (e.g., the hollow body 200). When closed, as shown, for example, in FIG. 14B, the flap 520 rests against the filter housing 510 and extends across the entirety of the face of the filter housing 510 so as to seal the face and prevent any backflow through the filter 540. In various embodiments, the body valve flap 520 opens when a sufficient pressure is created within the filter module 500, for example, as occurs when the piston 400 of the blood filtering apparatus 100 is pulled distally upward or outward away from the filter module 500. The body valve flap 520 closes when the pressure within the filter module 500 falls below a pressure threshold, for example, when the piston 400 of the blood filtering apparatus 100 is pushed proximally, towards the filter module 500. The flap 520 of various embodiments is a flexible material configured to minimize the pressure required to bend the flap open and enable forward flow through the filter 540.

In alternative embodiments of the apparatus 100, as shown for example in FIGS. 2, 4, 5A and 5B, the body valve controlling fluid flow into the hollow body 200 is separate from the filter module 500. In such embodiments, the body valve 220 preferably extends across the cross-section of the hollow body 200, such that the body valve 220 can form a substantially fluid-impermeable seal against the walls of the hollow body interior. The body valve 220 is preferably located within the hollow body 200, between the filter module 500 and the piston 400. The general body valve location is preferably maintained substantially static relative to the filter module 500 by the hollow body 200. For example, the body valve 220 of some embodiments rests within a groove defined on the interior wall of the hollow body 200. The body valve 220 is preferably a passive, one-way valve, but it can alternatively be an active valve (e.g., electrically driven), a two-way valve, or any other suitable valve. Examples of body valves 220 include switch body valves, duckbill valves, ball valves, or any other suitable valve.

The body valve 220/520 of various embodiments is preferably in an open position during the intake stroke, when negative pressure is applied to the hollow body interior. The body valve 220/520 is preferably in a closed position during the compression stroke, when positive pressure is applied to the hollow body interior, or when the hollow body interior pressure is substantially equal to the pressure of the ambient environment (e.g., when the piston 400 is at rest relative to the hollow body 200). By maintaining a closed position during the compression stroke, as shown in FIG. 5B, the body valve 220/520 can facilitate positive pressure generation within the hollow body volume, thus facilitating blood flow out of the hollow body 200 via the outlet 240. Alternatively, the body valve 220/520 can be in an open position during the compression stroke, when positive pressure is applied to the hollow body interior, wherein the blood within the hollow body 200 is egressed through the inlet 300. In another embodiment of the apparatus 100, the body valve 220/520 moves between the closed state to the open state during the intake stroke, and moves from the open state to the closed state during the compression stroke. The body valve 220/520 can alternatively have any other suitable configuration.

In some embodiments, the components of the apparatus 100 are made of materials that can withstand sterilization processes, such as heat sterilization, radiation sterilization, or chemical sterilization. Example sterilization processes include autoclaving, UV light exposure, or bleaching. Furthermore, the apparatus components are preferably made of one or more biocompatible materials, more preferably bio-inert materials. Example materials include Topas-Cyclic Olefin Copolymers (TCOC), Makrolon® (Bayer MaterialScience), polycarbonate, polyethylene terephthalate (PET), polytetrafluoroethylene (PTFE), polyethylene, polymethylmethacrylate (PMA), biocompatible polymers, biocompatible ceramics, and biocompatible metals, such as titanium, stainless steel. However, the apparatus components can be made of any suitable material. The apparatus components can additionally include a coating. In one variation of the apparatus, the coating can decrease blood clotting. In another variation of the apparatus, the coating is a biocompatible coating; this can be desirable if the apparatus component is made of a biologically incompatible material. The coating can include silicone, an anticoagulant coating (e.g., EDTA, citrate, oxlate, etc.), or any other suitable coating. The apparatus components are preferably injection molded, but can alternatively be sintered, stamped, or manufactured using any other suitable method.

Figure 15:
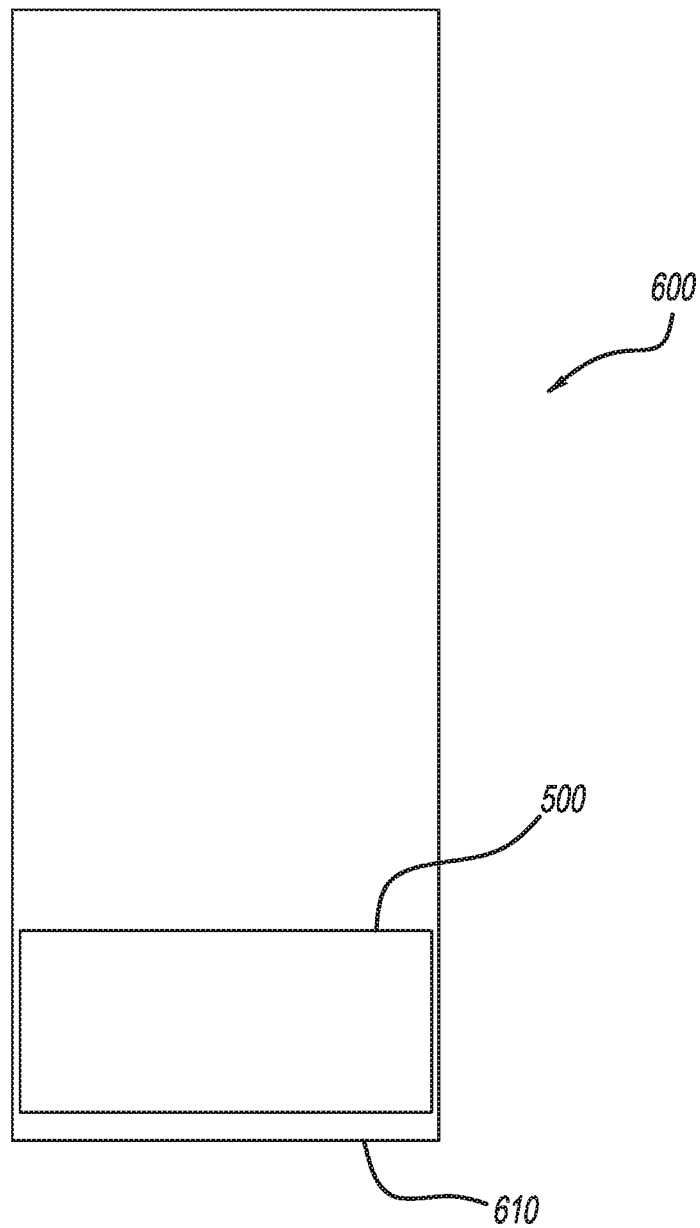
FIG. 15 illustrates a side view of one embodiment of a blood filtering apparatus formed of a fluid uptake device and a filter module.

In an alternative embodiment, the filtering module 500 described above may be used with an alternate blood filtering apparatus, such as the blood filtering apparatus of FIG. 15. As illustrated in FIG. 15, the blood filtering apparatus may be formed of any fluid uptake device 600 that has a fluid passageway 610 and an ability to create a negative internal pressure within the fluid passageway 610 so as to facilitate fluid uptake. For example, the uptake device 600 may be an eye dropper (i.e., a Pasteur pipette), with a deformable top. Alternatively, the uptake device 600 may be a straw, tube, or pipe. In such embodiments, negative internal pressure may be created by manually sucking on a distal end of the uptake device or by connecting the distal end to a pump, a vacuum, a deformable bulb, or other suitable device. In these alternative embodiments, the filtering module 500 may be sized to fit within the passageway 610 of the fluid uptake device 600.

In one embodiment of a method, the method includes providing a blood filtering apparatus. The blood filtering apparatus may have any or all of the features described elsewhere herein. As one non-limiting example, the apparatus includes a hollow body 200, a reservoir 320 with an inlet 300 connected to a hollow body 200 end, a piston 400 slidably disposed within the hollow body 200, and a filter module 500 within the hollow body 200 between the piston 400 and the inlet 300. The filter module 500 includes a filter 540 and a body valve 520. The hollow body 200 further includes outlet 240, and an outlet valve 242, and the reservoir 320 further includes an inlet valve 302. The reservoir 320 and hollow body 200 may be removably coupled by a bayonet locking mechanism or any other suitable connecting mechanism. The piston 400 includes a piston head 420 with substantially the same diameter as the inner diameter of the hollow body 200, a shaft 440 coupled to the piston head 420, and a handle 460 coupled to the shaft 440.

The method further includes moving the piston 400 through the intake stroke, wherein movement of the piston 400 through the intake stroke opens the inlet valve 302 and the body valve 520 and draws fluid (e.g., blood) through the inlet and the filter 540 into the hollow body 200. In flowing through the filter 540, the fluid is separated from undesired particulates in the fluid. For example, blood may enter into the hollow body 200, while the filter 540 blocks blood clots and large biological particulates from passing through to the hollow body. The body valve 520 may close upon completion of the intake stroke so as to prevent backflow of fluid through the filter 540. The method may additionally include moving the piston 400 through the compression stroke, wherein movement of the piston 400 through the compression stroke opens the outlet valve 242 and egresses fluid through the outlet 240. In some embodiments, a blood bag or transfusion tube is coupled to the outlet valve 242 prior to blood egress to collect the filtered blood. The valves are preferably all closed when the piston 400 is not translating.

In another embodiment, movement of the piston 400 through the intake stroke opens the inlet valve 302, body valve 520, and outlet valve 242, simultaneously drawing blood and fluid (e.g., anticoagulant solution) from the blood source (e.g., patient or collection volume) and coupled blood bag, respectively. Movement of the piston 400 through the compression stroke closes the inlet valve 302 and body valve 220 and opens the outlet valve 242, allowing blood egress out of the outlet 240 into the blood bag.

In another embodiment, movement of the piston 400 through the intake stroke opens the inlet valve 302 and the body valve 520, and draws blood through the filter into the hollow body volume. The piston 400 position is retained by the substantially equal force between the hollow body volume and the ambient environment. All valves are preferably closed when the piston 400 position is maintained. The reservoir 320 is decoupled from the hollow body 200 and the filter module 500 removed; the closed body valve 520 preferably maintains the hollow body volume sterility and pressure during this process. The reservoir 320 is then re-coupled to the hollow body 200, and movement of the piston 400 through the compression stroke opens the body valve 520 and egresses blood through the inlet 300. The original reservoir 320 can be used, a new filter module 500 can be installed, or a new reservoir 320 can be used for blood egress from the hollow body volume. This alternative can additionally include decoupling the piston 400 shaft 440 and handle 460 from the piston head 420 to retain the piston 400 position.

As used in the description and claims, the singular form "a", "an" and "the" include both singular and plural references unless the context clearly dictates otherwise. For example, the term "a filter" may include, and is contemplated to include, a plurality of filters. At times, the claims and disclosure may include terms such as "a plurality," "one or more," or "at least one;" however, the absence of such terms is not intended to mean, and should not be interpreted to mean, that a plurality is not conceived.

The term "about" or "approximately," when used before a numerical designation or range (e.g., to define a length or pressure), indicates approximations which may vary by (+) or (−) 5%, 1% or 0.1%. All numerical ranges provided herein are inclusive of the stated start and end numbers. The term "substantially" indicates mostly (i.e., greater than 50%) or essentially all of a device, substance, or composition.

As used herein, the term "comprising" or "comprises" is intended to mean that the devices, systems, and methods include the recited elements, and may additionally include any other elements. "Consisting essentially of" shall mean that the devices, systems, and methods include the recited elements and exclude other elements of essential significance to the combination for the stated purpose. Thus, a system or method consisting essentially of the elements as defined herein would not exclude other materials, features, or steps that do not materially affect the basic and novel characteristic(s) of the claimed invention. "Consisting of" shall mean that the devices, systems, and methods include the recited elements and exclude anything more than a trivial or inconsequential element or step. Embodiments defined by each of these transitional terms are within the scope of this disclosure.

The examples and illustrations included herein show, by way of illustration and not of limitation, specific embodiments in which the subject matter may be practiced. Other embodiments may be utilized and derived therefrom, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A removable filter module for a blood filtering apparatus, comprising:
    a filter housing formed of one or more side walls, the filter housing having a partially or fully open proximal face and distal face;
    a filter medium disposed within the filter housing, wherein the filter medium comprises a plurality of pores sized to prevent passage of blood clots and large biological particulates through the pores while permitting passage of blood cells through the pores;
    a body valve positioned on a proximal end of the filter housing, wherein the body valve is partially attached to the filter housing, the body valve being movable between an open and a closed configuration, wherein, in the closed configuration, the body valve seals an entire surface of the proximal face of the filter housing, and wherein, in the open configuration, the body valve bends such that one or more unattached portions of the body valve move outward away from the filter housing;
    an inlet positioned on a distal end of the body valve and configured to receive blood; and
    a hollow body positioned at a proximal end of the body valve and configured to store filtered blood.

2. The removable filter module of claim 1, wherein the filter module is sized and configured to fit securely within a blood filtering apparatus and to form a liquid-tight seal with an inner wall of the blood filtering apparatus.

3. The removable filter module of claim 2, wherein the body valve opens when a negative pressure is created within the blood filtering apparatus.

4. The removable filter module of claim 2, further comprising a sealing surface protruding from the one or more side walls of the filter housing, wherein the sealing surface is configured to compress against the inner wall of the blood filtering apparatus.

5. The removable filter module of claim 4, wherein the filter housing and the sealing surface are monolithic.

6. The removable filter module of claim 3, wherein the filter housing, the sealing surface, and the body valve are monolithic.

7. The removable filter module of claim 1, wherein the filter medium is formed of a membrane.

8. The removable filter module of claim 7, wherein the membrane comprises pleated triangle-shaped facets.

9. The removable filter module of claim 1, wherein the filter housing is cylindrical.

10. The removable filter module of claim 1, wherein the filter housing is transparent.

11. The removable filter module of claim 1, wherein the filter medium comprises a biocompatible material.

12. The removable filter module of claim 11, wherein the biocompatible material includes nylon or polyester.

13. A filter module, comprising:
    a filter medium comprising a plurality of pores sized to prevent passage of blood clots and large biological particulates through the pores while permitting passage of blood cells through the pores;
    an elastomeric housing disposed at least partially around the filter medium, the elastomeric housing having a partial or fully open proximal face and distal face, wherein the elastomeric housing comprises an inner column configured to create a hollow inner surface between a sidewall of the elastomeric housing and the inner column, wherein the elastomeric housing further comprises a sealing surface configured to create a seal between the filter module and a fluid uptake device configured to receive the filter module, and wherein the filter medium is positioned in a circle around the inner column; and a mechanical body valve positioned on the proximal face of the elastomeric housing configured to mechanically seal the proximal face of the filter module wherein the mechanical body valve comprises a flap, wherein the flap is partially attached to the elastomeric housing via a joint, and wherein the flap is configured to bend along the joint such that an unattached portion of the flap moves outward away from the elastomeric housing.

14. The filter module of claim 13, wherein the filter medium is formed of a membrane.

15. The filter module of claim 14, wherein the membrane comprises pleated triangle-shaped facets.

16. The filter module of claim 13, wherein the mechanical body valve opens to allow fluid to flow through the filter medium when subjected to a negative pressure and closes with ambient or positive pressure.

17. The filter module of claim 13, wherein the mechanical body valve closes when external pressure is applied on the filter module and opens when pressure within the filter module is increased.

18. A blood filtering apparatus, comprising:
a fluid uptake device comprising a fluid passageway; and
the filter module of claim 13 disposed within the passageway of the fluid uptake device.

19. The removable filter module of claim 13, wherein the filter medium is cylindrical.

* * * * *